(12) United States Patent
Ogino et al.

(10) Patent No.: US 9,895,320 B2
(45) Date of Patent: Feb. 20, 2018

(54) TRANSDERMAL PATCH WITH DIFFERENT VISCOSITY HYDROCARBON OILS IN THE DRUG LAYER AND THE ADHESIVE LAYER

(71) Applicant: KM TRANSDERM LTD., Osaka-shi, Osaka (JP)

(72) Inventors: Hiroyuki Ogino, Higashikagawa (JP);
Masaoki Goto, Higashikagawa (JP);
Atsuyo Hamada, Higashikagawa (JP);
Mitsuji Akazawa, Higashikagawa (JP);
Sadao Yukimoto, Higashikagawa (JP)

(73) Assignee: KM Transderm Ltd., Osaka (JP)

( * ) Notice: Subject to any disclaimer, the term of this patent is extended or adjusted under 35 U.S.C. 154(b) by 0 days.

(21) Appl. No.: 14/432,100

(22) PCT Filed: Sep. 28, 2013

(86) PCT No.: PCT/JP2013/076441
§ 371 (c)(1),
(2) Date: Jul. 6, 2015

(87) PCT Pub. No.: WO2014/051128
PCT Pub. Date: Apr. 3, 2014

(65) Prior Publication Data
US 2015/0374642 A1    Dec. 31, 2015

(30) Foreign Application Priority Data

Sep. 28, 2012  (JP) .................................. 2012-230284

(51) Int. Cl.
| | | |
|---|---|---|
| *A61K 9/70* | (2006.01) | |
| *A61K 31/325* | (2006.01) | |
| *A61K 31/4168* | (2006.01) | |
| *A61K 31/27* | (2006.01) | |
| *A61K 31/381* | (2006.01) | |
| *A61K 31/485* | (2006.01) | |
| *A61K 47/06* | (2006.01) | |
| *A61K 47/32* | (2006.01) | |
| *A61K 47/34* | (2017.01) | |

(52) U.S. Cl.
CPC ............ *A61K 9/7084* (2013.01); *A61K 31/27* (2013.01); *A61K 31/325* (2013.01); *A61K 31/381* (2013.01); *A61K 31/4168* (2013.01); *A61K 31/485* (2013.01); *A61K 47/06* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,201,211 A | 5/1980 | Chandrasekaran et al. | |
| 6,335,031 B1 | 1/2002 | Asmussen et al. | |
| 6,517,964 B2 | 2/2003 | Mercuri | |
| 6,689,379 B1 | 2/2004 | Bracht | |
| 2001/0048938 A1 | 12/2001 | Asmussen et al. | |
| 2007/0104773 A1* | 5/2007 | So .................... | A61K 8/0208 424/449 |
| 2007/0128263 A1 | 6/2007 | Gargiulo et al. | |
| 2007/0255197 A1* | 11/2007 | Humberstone ....... | A61K 9/7023 604/30 |
| 2012/0029446 A1* | 2/2012 | Amano ................ | A61K 9/7084 604/304 |
| 2013/0226112 A1 | 8/2013 | Akazawa et al. | |
| 2013/0266633 A1 | 10/2013 | Gargiulo et al. | |
| 2014/0134230 A1 | 5/2014 | Frank et al. | |
| 2014/0303189 A1 | 10/2014 | Goto et al. | |

FOREIGN PATENT DOCUMENTS

| | | | |
|---|---|---|---|
| JP | S62-014526 B2 | 4/1987 | |
| JP | H09-291028 A | 11/1997 | |
| JP | H09-315957 A | 12/1997 | |
| JP | H10-316559 A | 12/1998 | |
| JP | 2001-302502 A | 10/2001 | |
| JP | 2002-500178 A | 1/2002 | |
| JP | 2002-542277 A | 12/2002 | |
| JP | 2003-063954 A | 3/2003 | |
| JP | 2009-517468 A | 4/2009 | |
| WO | WO 1999/034782 A1 | 7/1999 | |
| WO | WO 2000/012070 A1 | 3/2000 | |
| WO | WO 2007/064407 A1 | 6/2007 | |
| WO | WO 2010/095537 * | 8/2010 | ............. A61K 47/34 |
| WO | WO 2012/029325 A1 | 3/2012 | |

(Continued)

OTHER PUBLICATIONS

Japanese Patent Office, International Search Report in International Patent Application PCT/JP2013/076441 (dated Nov. 19, 2013).
Boehringer Ingelheim, "Catapres-TTS® Transdermal Therapeutic System" Prescribing Information and Patient Instructions (May 2012).

(Continued)

*Primary Examiner* — Kevin S Orwig
(74) *Attorney, Agent, or Firm* — Leydig, Voit & Mayer, Ltd.

(57) ABSTRACT

A patch containing a storage layer retaining a drug or a pharmaceutically acceptable salt thereof and an adhesive layer which are formed on a support, wherein the adhesive layer contains a thermoplastic elastomer, and a non-volatile hydrocarbon oil in more than 50 parts by weight and not more than 800 parts by weight per 100 parts by weight of the elastomer, and the adhesive layer optionally further contains a tackifier at a content of not more than 10 wt %.

13 Claims, 2 Drawing Sheets

(56) References Cited

FOREIGN PATENT DOCUMENTS

WO     WO 2012/087047     *   6/2012    ............... A61K 9/70
WO     WO 2013/027681 A1     2/2013

OTHER PUBLICATIONS

The International Bureau of WIPO, Written Opinion of The International Searching Authority in International Patent Application No. PCT/JP2013/076441 (dated Mar. 31, 2015).

* cited by examiner

TRANSDERMAL PATCH WITH DIFFERENT VISCOSITY HYDROCARBON OILS IN THE DRUG LAYER AND THE ADHESIVE LAYER

CROSS-REFERENCE TO RELATED APPLICATIONS

This patent application is the U.S. national phase of International Application No. PCT/JP2013/076441, filed on Sep. 28, 2013, which claims the benefit of Japanese Patent Application No. 2012-230284, filed Sep. 28, 2012, which are incorporated by reference in their entireties herein.

TECHNICAL FIELD

The present invention relates to a patch containing a drug. More particularly, the present invention relates to a patch which shows high skin permeability of a drug, good transdermal absorbability and low skin irritation.

BACKGROUND ART

When transdermal absorption of a drug is desired, the drug is added to an adhesive matrix and the like and a patch is formed. In recent years, a tape agent more superior in the adhesiveness is more often used than cataplasm containing a large amount of water as a constituent component in the patch. As the adhesive matrix for this tape agent, lipophilic adhesive matrices such as rubber-based, acrylic-based, silicone-based and the like are used.

However, in what is called a "matrix type patch" wherein a drug is directly mixed with an adhesive matrix, a usable preparation sometimes cannot be achieved when a large amount of a drug is contained and the like, since the drug cannot be completely enclosed and exudes out, and adhesiveness decreases.

On the other hand, rivastigmine, i.e., 3-[(1S)-1-(dimethylamino)ethyl]phenyl N-ethyl-N-methylcarbamate, is known as a therapeutic drug for of Alzheimer-type dementia, and the effect thereof is considered to be mainly attributable to the inhibition of acetylcholinesterase and butyrylcholinesterase, which increases intracerebral acetylcholine and activates the intracerebral cholinergic nerve system.

As a patch containing rivastigmine, a transdermal absorption type preparation containing rivastigmine together with an antioxidant in an adhesive substrate composed of polyacrylate or polymethacrylate (patent document 1) is known. However, such preparation has a problem of the aforementioned low adhesiveness and, as a remedy, a transdermal absorption type preparation comprising a backing layer (support), a rivastigmine storage layer containing polymers such as polyacrylate, polymethacrylate, polyisobutylene, polybutene, styrene-isoprene-styrene block copolymer and the like and rivastigmine, and an adhesion layer containing a silicone polymer and a tackifier has been proposed (patent document 2).

"EXELON PATCH", which is a patch of rivastigmine, has been placed in the market. As mentioned above, it is a transdermal absorption type preparation comprising a rivastigmine storage layer, and an adhesion layer containing a silicone polymer and a tackifier, which has adhesiveness sufficient for use. This patch has many advantages afforded by not being orally ingested, that side effects such as vomiting and the like can be suppressed, a rapid increase in the blood concentration can be suppressed and the like, since rivastigmine does not go into the stomach directly unlike oral drugs.

However, in the domestic clinical tests of EXELON PATCH, an adverse event such as skin reaction and stimulation at the application site was seen in 663 cases (77.3%) out of 858 cases as the safety analysis subjects, and the skin irritation at the application site poses a problem (non-patent document 1). In particular, many of the Alzheimer-type dementia patients are old. The skin of old person is prone to express skin symptoms more often, since it shows low moisturizing function, gets dry and highly likely shows low skin barrier function due to a decreased production quantity of sebum. Therefore, when a patch showing skin irritation is adhered to the aged patients, the possibility is extremely high that some harmful phenomenon occurs on the skin. Examples of other existing preparations composed of a medicament storage layer and an adhesion layer include buprenorphine (analgesis of chronic pain) preparations, and clonidine (therapeutic drug for hypertension) preparations. These two preparations have problems in skin irritation (non-patent documents 2, 3).

On the other hand, as a matrix type transdermal absorption type preparation containing a drug other than rivastigmine, for example, a patch using a rubber-based, acrylate-based or silicone-based adhesive matrix is disclosed as a preparation of tolterodine, an antimuscarinic drug (patent document 3). From the aspect of drug stability, moreover, a patch using a rubber-based adhesive (rubber-based adhesive matrix) showing less interaction with drugs has been proposed (patent documents 4-6). Also in these matrix type preparations, for example, skin irritation at application site has become a problem in Rotigotine (therapeutic drug for Parkinson's disease) preparation and the like (non-patent document 4).

DOCUMENT LIST

Patent Documents patent document 1: WO99/034782
patent document 2: WO2007/064407
patent document 3: WO2000/12070
patent document 4: JP-A-2001-302502
patent document 5: JP-A-9-291028
patent document 6: JP-A-10-316559
patent document 7: JP-B-62-14526

Non-Patent Documents non-patent document 1: pharmaceutical product interview form "EXELON PATCH" (rivastigmine transdermal absorption type preparation); revised in July 2011
non-patent document 2: pharmaceutical product interview form "NORSPAN TAPE" (buprenorphine transdermal absorption type preparation); revised in August 2013
non-patent document 3: Label "Catapres-TTS"; revised in May 2012
non-patent document 4: pharmaceutical product interview form "NEUPRO PATCH" (Rotigotine transdermal absorption type preparation); January 2012, first edition

SUMMARY OF THE INVENTION

Problems to be Solved by the Invention

The present inventors tried to develop a patch containing rivastigmine as a drug by using, for example, the adhesive layer components described in patent documents 3-6. However, it was clarified that a patch having an adhesive layer containing a rubber-based adhesive matrix and the like cannot ensure sufficient releasability of rivastigmine. Also, it was clarified that the aforementioned patch generally requires addition of a tackifier to impart sufficient skin adhesiveness, and the tackifier causes skin irritation.

In view of the above-mentioned problems and the like, an object of the present invention is to provide a patch having sufficient skin adhesiveness and low skin irritation, showing good skin permeability of the drug, and sufficient transdermal absorbability.

Means of Solving the Problems

The present inventors have conducted intensive studies in an attempt to solve the aforementioned problems and successfully reduced skin irritation while ensuring sufficient skin adhesiveness in a patch containing a drug storage layer and an adhesive layer, by using, as components for forming an adhesive layer, a thermoplastic elastomer and a non-volatile hydrocarbon oil at a particular weight ratio relative to the elastomer, and reducing the content of tackifier. Furthermore, the drug showed good skin permeability and sufficient transdermal absorbability, which resulted in the completion of the present invention.

Therefore; the present invention relates to the following [1]-[9].
[1] A patch comprising a storage layer retaining a drug or a pharmaceutically acceptable salt thereof and an adhesive layer which are formed on a support, wherein
the adhesive layer comprises at least
a thermoplastic elastomer, and
a non-volatile hydrocarbon oil in more than 50 parts by weight and not more than 800 parts by weight per 100 parts by weight of the thermoplastic elastomer, and
the adhesive layer optionally further comprises a tackifier at a content of not more than 10 wt %.
[2] The patch of the above-mentioned [1], wherein the content of the non-volatile hydrocarbon oil in the adhesive layer is not less than 23.5 wt % and not more than 88 wt %.
[3] The patch of the above-mentioned [1] or [2], wherein the non-volatile hydrocarbon oil is liquid paraffin.
[4] The patch of any one of the above-mentioned [1]-[3], wherein the thermoplastic elastomer is a styrene-based block copolymer.
[5] The patch of the above-mentioned [4], wherein the styrene-based block copolymer is a styrene-isoprene-styrene block copolymer.
[6] The patch of any one of the above-mentioned [1]-[5], wherein the adhesive layer is free of a tackifier.
[7] The patch of any one of the above-mentioned [1]-[6], wherein the drug is one or more kinds selected from the group consisting of rivastigmine, clonidine, Rotigotine and buprenorphine.
[8] The patch of any one of the above-mentioned [1]-[6], wherein the drug is clonidine or rivastigmine.
[9] The patch of any one of the above-mentioned [1]-[6], wherein the drug is rivastigmine.

Effect of the Invention

The patch of the present invention shows good skin permeability of a drug and superior transdermal absorbability. Also, it has sufficient adhesiveness when adhered to the skin and causes low skin irritation.

DESCRIPTION OF EMBODIMENTS

Figure 1:
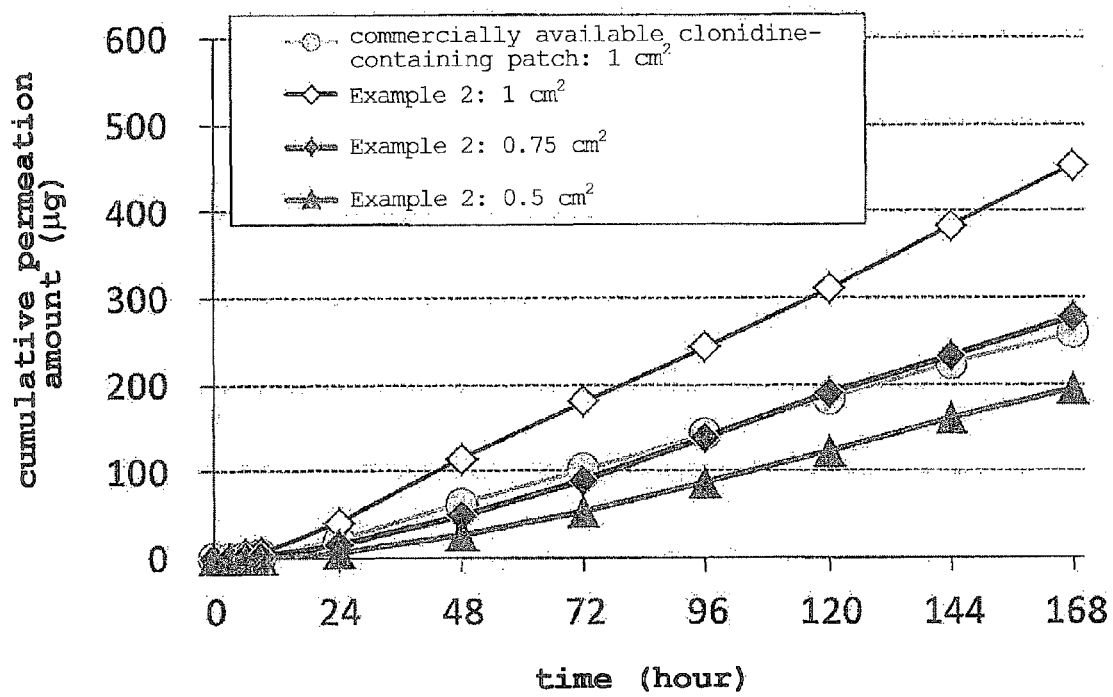
FIG. 1 shows a cumulative permeation amount of clonidine that permeated the rat skin in the skin permeability test in Experimental Example 2.

The patch of the present invention is mainly characterized in that it comprises a storage layer retaining a drug or a pharmaceutically acceptable salt thereof and an adhesive layer which are formed on a support (hereinafter to be also referred to as a "drug storage layer"), wherein
the adhesive layer comprises at least
a thermoplastic elastomer, and
a non-volatile hydrocarbon oil in more than 50 parts by weight and not more than 800 parts by weight per 100 parts by weight of the thermoplastic elastomer, and
the adhesive layer optionally further comprises a tackifier at a content of not more than 10 wt %.

The patch of the present invention basically takes a laminate constitution of support/drug storage layer/adhesive layer and optionally has, where/necessary, a drug permeation control film between a drug storage layer and an adhesive layer.

In the patch of the present invention, the drug to be transdermally absorbed is not particularly limited and, for example, those described in patent document 2 can be mentioned. Preferably, rivastigmine, clonidine, Rotigotine, buprenorphine and the like having a problem of skin irritation in existing preparations can be mentioned, more preferably, rivastigmine and clonidine whose existing preparations are patches having a drug storage layer and an adhesive layer, particularly preferably rivastigmine.

In the patch of the present invention, the drug to be transdermally absorbed may be a free form (free base) or a pharmaceutically acceptable salt. Examples of the salt include acid addition salts and salts with base, and examples of the acid addition salt include salts with organic acid such as monocarboxylic acid (acetic acid, propionic acid, butyric acid and the like); dicarboxylic acid (oxalic acid, malonic acid, fumaric acid, succinic acid, maleic acid and the like); hydroxycarboxylic acid (hydroxyacetic acid, lactic acid, malic acid, citric acid, tartaric acid and the like); carbonic acid; alkanesulfonic acid (methanesulfonic acid, ethanesulfonic acid and the like); amino acid such as glutamic acid and the like, and the like, salts with inorganic acids such as hydrochloric acid, hydrobromic acid, sulfuric acid, nitric acid, phosphoric acid and the like, and the like. Examples of the salt with base include salt with inorganic base such as sodium salt, potassium salt, calcium salt, magnesium salt and the like, and salt with organic base such as piperidine, morpholine, pyrrolidine, arginine, lysine and the like. The free form (free base) and the salt may be each a hydrate. From the aspects of dispersibility in a drug storage layer and transdermal absorbability, the drug is preferably a free form (free base). From the aspects of easy availability, dispersibility in the adhesive layer and the like, the salt of rivastigmine is preferably rivastigmine tartrate. The salt of clonidine and buprenorphine is preferably hydrochloride, and Rotigotine is preferably in a free form (free base).

In the present invention, one or more kinds of drugs or a pharmaceutically acceptable salt thereof can be used.

While the content of the drug in the patch of the present invention is not particularly limited, in consideration of drug dispersibility and transdermal absorbability in the drug storage layer, it is preferably 1 wt %-30 wt %, more preferably 2.5 wt %-25 wt %, most preferably 4 wt %-20 wt %, of the drug storage layer. The adhesive layer may also contain a drug as long as the adhesiveness is not prevented. When the adhesive layer contains a drug, the content is preferably 0 wt %-15 wt %, more preferably 0 wt %-10 wt %, most preferably 0 wt %-5 wt %, of the adhesive layer.

The patch of the present invention contains a thermoplastic elastomer in the adhesive layer.

The "thermoplastic elastomer" is an elastomer having thermoplasticity wherein it is softened when heat is added to show flowability, and returns to a rubbery elastic body by cooling, and various thermoplastic elastomers of urethane, acrylic, styrene, olefin series and the like can be mentioned. Particularly, styrene thermoplastic elastomer, especially styrene-based block copolymer, is preferably used to simultaneously achieve sufficient skin adhesiveness and low skin irritation, which is the object of the present invention.

Specific examples of the styrene-based block copolymer include styrene-butadiene block copolymer, styrene-butadiene-styrene block copolymer, styrene-isoprene block copolymer, styrene-isoprene-styrene block copolymer, styrene-ethylene/butylene block copolymer, styrene-ethylene/butylene-styrene block copolymer, styrene-ethylene/propylene block copolymer, styrene-ethylene/propylene-styrene block copolymer, styrene-isobutylene block copolymer, styrene-isobutylene-styrene block copolymer and the like. In the above, "ethylene/butylene" shows an ethylene and butylene copolymer block, and "ethylene/propylene" shows an ethylene and propylene copolymer block. One or more kinds of these styrene block copolymers can be used.

From the aspects of simultaneously achievement of sufficient skin adhesiveness and low skin irritation, and availability and handling property of the products for patch, of the above-mentioned styrene-based block copolymers, a styrene-isoprene-styrene block copolymer and a styrene-isoprene block copolymer are preferably used. Particularly, a mixture of a styrene-isoprene-styrene block copolymer and a styrene-isoprene block copolymer is preferably used from the aspect of adhesiveness. When the mixing ratio of the styrene-isoprene block copolymer in the mixture is too low, skin adhesiveness tends to decrease. When it is too high, shape retention of the adhesive layer tends to be degraded, which in turn may cause inconveniences on adhesion to the skin, such as adhesive residue on the skin after peeling off and the like. Therefore, the mixing ratio of the styrene-isoprene-styrene block copolymer and the styrene-isoprene block copolymer in weight ratio is preferably 10/90-82/18, more preferably 20/80-75/25, further preferably 30/70-70/30.

For the object of the present invention, a styrene-isoprene-styrene block copolymer preferably has a content of the styrene in the copolymer of 5 wt %-60 wt %, more preferably 10 wt %-50 wt %. In addition, it preferably has a weight average molecular weight as measured by gel filtration chromatography of 20,000-500,000, more preferably 30,000-300,000. As the styrene-isoprene block copolymer, one having a content of the styrene in the copolymer of 5 wt %-50 wt %, more preferably 10 wt %-40 wt %. In addition, it preferably has a weight average molecular weight as measured by gel filtration chromatography of 10,000-500,000, more preferably 20,000-300,000. The mixture of the styrene-isoprene-styrene block copolymer and the styrene-isoprene block copolymer preferably has a weight average molecular weight as measured by gel filtration chromatography of 20,000-500,000, more preferably 30,000-300,000.

As the styrene-isoprene-styrene block copolymer and the styrene-isoprene block copolymer, copolymers produced by a method known per se can be respectively used. As the styrene-isoprene-styrene block copolymer and the styrene-isoprene block copolymer, commercially available products that satisfy the above-mentioned copolymer compositions and molecular weight properties can be respectively used. In addition, a mixture of the styrene-isoprene-styrene block copolymer and the styrene-isoprene block copolymer is also commercially available, and a commercially available product of a mixture of the styrene-isoprene-styrene block copolymer and the styrene-isoprene block copolymer at the above-mentioned mixing ratio can satisfy the above-mentioned copolymer compositions and molecular weight properties can be preferably used, respectively.

Examples of such commercially available product include "KRATON D1161", "KRATON D1163", "KRATON D1113" and "KRATON D1119" manufactured by KRATON POLYMERS, "JSR SIS5229", "JSR SIS5403" and "JSR SIS5505" manufactured by JSR and the like.

When the content of the thermoplastic elastomer in the adhesive layer is too small, the shape of the adhesive layer is difficult to maintain, and when it is too much, skin adhesiveness becomes insufficient. Therefore, the content of the thermoplastic elastomer in the adhesive layer of the patch of the present invention is preferably 8 wt %-66 wt %, more preferably 10 wt %-65 wt %, particularly preferably 12 wt %-64 wt %, relative to the whole adhesive layer.

In the patch of the present invention, the adhesive layer contains non-volatile hydrocarbon oil.

As the non-volatile hydrocarbon oil, a chain saturated hydrocarbon having about 20-40 carbon atoms or a chain unsaturated hydrocarbon having about 20-40 carbon atoms is preferable and, for example, liquid paraffin, squalene, squalene, pristine and the like can be mentioned. In view of easy availability, liquid paraffin is more preferable. Liquid paraffin is a mixture of colorless odorless liquid alkane having not less than 20 carbon atoms. In the present invention, liquid paraffin compatible with the standard defined in the Japanese Pharmacopoeia, United States Pharmacopoeia and the like, and the like can be preferably used. The non-volatile hydrocarbon oil having high viscosity is preferable, and liquid paraffin having high viscosity is particularly preferably used from the aspect of adhesiveness. To be specific, the non-volatile hydrocarbon oil preferably shows kinematic viscosity at 40° C. of not less than 60 mm$^2$/s, more preferably not less than 70 mm$^2$/s, particularly preferably not less than 80 mm$^2$/s. While the upper limit of the kinematic viscosity is not particularly limited, it is, for example, preferably not more than 500 mm$^2$/s, more preferably not more than 250 mm$^2$/s, from the aspects of easy handling, easy availability and the like.

The adhesive layer contains the above-mentioned non-volatile hydrocarbon oil at a weight ratio of more than 50 parts by weight and not more than 800 parts by weight, relative to 100 parts by weight of the thermoplastic elastomer. When the content of the non-volatile hydrocarbon oil relative to 100 parts by weight of the thermoplastic elastomer is more than 800 parts by weight, shape retention of the adhesive layer becomes difficult. On the other hand, when the content of the non-volatile hydrocarbon oil is not more than 50 parts by weight, the adhesive becomes too hard and sufficient skin adhesiveness tends to be unachieved. Particularly, the followability to the moving skin during adhesion becomes poor, thus resulting in possible falling off during application. From such aspect, the content of the non-volatile hydrocarbon oil in the adhesive layer is preferably 51 parts by weight-800 parts by weight, more preferably 60 parts by weight-600 parts by weight, most preferably 70 parts by weight-500 parts by weight, relative to 100 parts by weight of the thermoplastic elastomer.

The content of the non-volatile hydrocarbon oil in the adhesive layer is preferably 23.5 wt %-88 wt %, more preferably 25 wt %-85 wt %, most preferably 26.5 wt %-83 wt %.

In the patch of the present invention, a thermoplastic elastomer and a non-volatile hydrocarbon oil are contained at the contents and content ratio as mentioned above to give an adhesive layer, whereby good skin adhesiveness can be exhibited. The adhesive layer may contain a tackifier as necessary.

Here, the tackifier is a resin generally used widely to impart skin adhesiveness in the field of patches, and examples thereof include rosin resin, polyterpene resin, coumarone-indene resin, petroleum resin, terpene-phenol resin, alicyclic saturated hydrocarbon resin and the like. One or more kinds therefrom can be used.

However, from the aspects of reduction of skin irritation and the like, the content of the tackifier in the adhesive layer is not more than 10 wt % in the present invention. The content is preferably not more than 5 wt %, more preferably not more than 2 wt %, further preferably not more than 1 wt %, and most preferably none. From the relationship with the skin adhesiveness of the patch, the content of the tackifier is adjusted according to the kind, content, and content ratio of the thermoplastic elastomer and non-volatile hydrocarbon oil.

While the thickness of the adhesive layer in the patch of the present invention is not particularly limited, to maintain adhesiveness sufficient for adhesion and not prevent permeation of a drug, it is preferably 10-2000 μm, more preferably 20-1000 μm. In addition, the mass per unit area of the adhesive layer is preferably 10 g/m$^2$-1,000 g/m$^2$, more preferably 20 g/m$^2$-800 g/m$^2$.

The constituent component (component other than drug) of the drug storage layer of the patch of the present invention is not particularly limited, and examples thereof include constituent components (various polymer components etc.) of the drug storage layer described in patent document 2 and patent document 7. In addition, the "thermoplastic elastomer" and "non-volatile hydrocarbon oil" used for the aforementioned "adhesive layer" can also be used as constituent components of the drug storage layer, and a patch comprising a drug storage layer containing such "thermoplastic elastomer" and "non-volatile hydrocarbon oil" is one preferable embodiment of the patch of the present invention. The content of the thermoplastic elastomer in the drug storage layer is preferably 8 wt %-66 wt %, more preferably 10 wt %-65 wt %, particularly preferably 12 wt %-64 wt %. The non-volatile hydrocarbon oil is preferably used at a ratio of 10-1200 parts by weight, more preferably 50-800 parts by weight, per 100 parts by weight of the thermoplastic elastomer. The "non-volatile hydrocarbon oil" having a comparatively low viscosity can also be used preferably for the drug storage layer, and on having a kinematic viscosity at 40° C. of less than 60 mm$^2$/s can also be used. As liquid paraffin, what is called light liquid paraffin (liquid paraffin having kinematic viscosity (37° C.) of less than 37 mm$^2$/s as defined in the Japanese Pharmacopoeia, liquid paraffin having kinematic viscosity (37° C.) of less than 34.5 mm$^2$/s as defined in the US Pharmacopoeia) may also be used.

To increase the dispersibility and transdermal absorbability of a drug in the drug storage layer, the drug storage layer may further contain an organic solvent such as alcohol solvent, amide solvent, ester solvent and the like; liquid organic acid; carboxylic acid salt; lactone; surfactant and the like.

Examples of the alcohol solvent include higher saturated aliphatic alcohol having about 12-20 carbon atoms which is liquid at ambient temperature, such as lauryl alcohol, isostearyl alcohol, 2-octyldodecanol and the like; higher unsaturated aliphatic alcohol having about 12-20 carbon atoms which is liquid at ambient temperature, such as oleyl alcohol and the like; polyvalent alcohol which is liquid at ambient temperature such as ethylene glycol, propylene glycol, glycerol, 1,3-butanediol, polyethylene glycol having a molecular weight of about 100-600 and the like; and the like. The "ambient temperature" in the present specification is within the range of 15-25° C. in the principles of the Japanese Pharmacopoeia.

Of these, polyvalent alcohol which is liquid at ambient temperature such as ethylene glycol, propylene glycol, glycerol, 1,3-butanediol, polyethylene glycol and the like is preferable, diol which is liquid at ambient temperature such as ethylene glycol, propylene glycol, 1,3-butanediol, polyethylene glycol having a molecular weight of about 100-600 and the like are more preferable to improve the solubility of a drug.

One or more kinds of alcohol solvents can be used.

Examples of the amide solvent include pyrrolidones such as N-methyl-2-pyrrolidone, 2-pyrrolidone and the like; imidazolidinones such as 1,3-dimethyl-2-imidazolidinone and the like; N-substituted toluidines such as crotamiton and the like; alkaneamides such as formamide, N-methylformamide, N,N-dimethylformamide, N-methylacetamide, N,N-dimethylacetamide, N-methylpropaneamide and the like, and the like.

Among the above-mentioned amide solvents, N-methyl-2-pyrrolidone, crotamiton, N,N-dimethylformamide and N,N-dimethylacetamide are preferable, and N-methyl-2-pyrrolidone and crotamiton are more preferable, to improve solubility, dispersibility and transdermal absorbability of a drug (particularly rivastigmine).

One or more kinds of amide solvents can be used.

Examples of an ester solvent include ester of long chain fatty acid and monovalent aliphatic alcohol, medium-chain triglyceride, ester of polyvalent carboxylic acid and monovalent aliphatic alcohol, carbonate and the like.

As an ester of long chain fatty acid and monovalent aliphatic alcohol, an ester, which is liquid at ambient temperature, of long chain saturated fatty acid having 12-20 carbon atoms and monovalent aliphatic alcohol having 1-20 carbon atoms is preferable, and examples thereof include myristates such as ethyl myristate, isopropyl myristate, octyldodecyl myristate and the like, palmitate which is liquid at ambient temperature such as ethyl palmitate, isopropyl palmitate, isostearyl palmitate and the like, stearate which is liquid at ambient temperature such as isopropyl stearate and the like, and the like. In addition, an ester of long-chain unsaturated fatty acid having 12-20 carbon atoms and monovalent aliphatic alcohol having 1-20 carbon atoms can also be used preferably, and examples thereof include oleate which is liquid at ambient temperature such as ethyl oleate, decyl oleate, oleyl oleate and the like, linoleate which is liquid at ambient temperature such as ethyl linoleate, isopropyl linoleate and the like, and the like.

Medium-chain triglyceride is a triglyceride of fatty acid having about 6-12 carbon atoms such as caproic acid, caprylic acid, capric acid, lauric acid and the like, and glycerol. In the present invention, caprylic acid triglyceride, a triglyceride mixture of caprylic acid and capric acid, a triglyceride mixture of caprylic acid, capric acid and lauric acid, and the like, which are liquid at ambient temperature, can be preferable. In addition, fats and oils containing a large amount of these, which are liquid at ambient temperature, can also be particularly preferable. Examples of such fats and oils include peanuts oil, olive oil, castor oil and the like.

As medium-chain triglyceride which is liquid at ambient temperature or medium-chain triglyceride containing fats and oils, which is liquid at ambient temperature, a commercially available product for pharmaceutical use can also be used.

Examples of the ester of polyvalent carboxylic acid and monovalent aliphatic alcohol include diester, which is liquid at ambient temperature, of dicarboxylic acid having 2-12 carbon atoms and monovalent aliphatic alcohol having 1-20 carbon atoms such as adipic acid diester which is liquid at ambient temperature such as, preferably, diethyl adipate, diisopropyl adipate and the like, sebacic acid diester which is liquid at ambient temperature such as diethyl sebacate, diisopropyl sebacate, dioctyldodecyl sebacate and the like, and the like.

Examples of carbonate include cyclic carbonate of carbonic acid and diol having 2-10 carbon atoms, such as ethylene carbonate, propylene carbonate, vinylene carbonate and the like, with preference given to propylene carbonate.

Of the ester solvents, myristate, a medium-chain triglyceride mixture, sebacic acid diester and carbonate are preferable. Particularly preferable examples thereof include isopropyl myristate, a triglyceride mixture of caprylic acid and capric acid, diethyl sebacate and propylene carbonate.

One or more kinds of ester solvents can be used.

In the present invention, one or more kinds selected from alcohol solvents, amide solvents and ester solvents can be used.

The content of the organic solvent in the drug storage layer is preferably 0.1 wt %-20 wt %, more preferably 0.5 wt %-15 wt %, of the total amount of the drug storage layer.

Examples of the liquid organic acid include aliphatic monocarboxylic saturated acids such as acetic acid, propionic acid, butyric acid, valeric acid, isovaleric acid, caproic acid, enanthic acid (heptanoic acid), caprylic acid, pelargric acid (nonanoic acid) and the like; aliphatic unsaturated monocarboxylic acids such as oleic acid, linoleic acid, arachidonic acid, docosahexaenoic acid and the like; hydroxycarboxylic acids such as lactic acid (DL-lactic acid, a mixture of L-lactic acid and/or D-lactic acid and anhydrous lactic acid) and the like; liquid carboxylic acids substituted by an alkoxy group such as methoxyacetic acid and the like; organic sulfonic acids such as methanesulfonic acid and the like, and the like.

The liquid organic acid has a function to aid dissolution of a drug and, as a result, a low-soluble drug can be contained in the drug storage layer at a high concentration, as well as dispersibility can also be improved, and further, transdermal absorbability can be improved. From such aspects, of the liquid organic acids, the Japanese Pharmacopoeia lactic acid and oleic acid are preferably used, and the Japanese Pharmacopoeia lactic acid is particularly preferably used.

One or more kinds of liquid organic acid can be used. The content of the liquid organic acid is preferably 0.1 wt %-20 wt %, more preferably 0.5 wt %-15 wt %, of the total amount of the drug storage layer.

Examples of the carboxylic acid salt include carboxylic acid salts of aliphatic monocarboxylic acid, alicyclic monocarboxylic acid, aliphatic dicarboxylic acid and the like.

Examples of aliphatic monocarboxylic acid include short chain fatty acids having 2-7 carbon atoms such as acetic acid, butyric acid, hexanoic acid and the like, middle chain fatty acids having 8-11 carbon atoms such as octanoic acid, decanoic acid and the like, long chain fatty acids having 12 or more carbon atoms such as myristic acid, stearic acid, isostearic acid, oleic acid and the like, hydroxymonocarboxylic acids such as glycolic acid, lactic acid, 3-hydroxybutyric acid, mandelic acid and the like, alkoxy group-substituted monocarboxylic acids such as methoxyacetic acid and the like, ketomonocarboxylic acids such as levulinic acid and the like, and the like.

Examples of alicyclic monocarboxylic acid include alicyclic monocarboxylic acids having 6-8 carbon atoms such as cyclohexane carboxylic acid and the like.

Examples of aliphatic dicarboxylic acid include sebacic acid, adipic acid, malic acid, maleic acid, fumaric acid and the like.

Carboxylic acid is preferably long chain fatty acid having 12 or more carbon atoms or hydroxymonocarboxylic acid, more preferably myristic acid, stearic acid, isostearic acid, oleic acid or lactic acid, particularly preferably oleic acid or lactic acid.

Examples of the carboxylic acid salt include alkali metal salts such as sodium salt, potassium salt and the like, alkaline earth metal salts such as calcium salt and the like, amine salt and the like. It is preferably sodium salt from the aspects of easy availability, stability and transdermal absorbability improving effect.

Carboxylic acid salt is preferably sodium oleate or sodium lactate from the aspects of drug stability improving effect and transdermal absorbability improving effect.

One or more kinds of carboxylic acid salt can be used. The content of the carboxylic acid salt is preferably not less than 0.1 mol and not more than 5 mol, more preferably not less than 0.2 mol and not more than 3 mol, per 1 mol of a drug in the drug storage layer. When the amount is less than 0.1 mol relative to 1 mol of the drug, a sufficient transdermal absorbability improving effect sometimes cannot be achieved. When the amount is more than 5 mol relative to 1 mol of the drug, the properties of preparation such as adhesive property and the like are sometimes degraded.

Examples of lactone include 5-membered ring lactone such as ascorbic acid, isoascorbic acid and the like, and the like.

One or more kinds of lactone can be used. The content of lactone is preferably not less than 0.1 mol and not more than 5 mol, more preferably not less than 0.2 mol and not more than 3 mol, per 1 mol of a drug in the drug storage layer. When it is less than 0.1 mol per 1 mol of a drug, a sufficient transdermal absorbability improving effect sometimes cannot be achieved, and when it is more than 5 mol per 1 mol of a drug, preparation properties such as adhesive property and the like may be deteriorated.

Examples of the surfactant include non-ionic surfactants such as polyoxyethylene fatty acid esters such as polyoxyethylene monolaurate and the like, polyoxyethylene sorbit fatty acid esters such as polyoxyethylene sorbit tetraoleate and the like, polyoxyethylene sorbitan ester of fatty acids such as polyoxyethylene sorbitan monooleate, polyoxyethylene sorbitan monolaurate, polyoxyethylene sorbitan monopalmitate and the like, sorbitan ester of fatty acids such as sorbitan monolaurate, sorbitan monooleate, sorbitan sesquioleate, sorbitan trioleate and the like, fatty acid esters of glycerol such as glycerol monooleate, polyoxyethylene castor oil derivative, polyoxyethylene hydrogenated castor oil and the like, polyoxyethylene higher aliphatic alcohol ethers such as polyoxyethylene lauryl ether, polyoxyethylene oleyl ether and the like, polyoxyethylene alkyl phenyl ethers such as polyoxyethylene nonyl phenyl ether and the like, polyoxyethylene polyoxypropylene copolymer such as pluronic L-31, pluronic L-44 and the like, and the like, anionic surfactants such as sodium alkylsulfates (e.g., sodium lauryl sulfate and the like) and the like, cationic surfactants such as alkyl trimethyl ammonium salt, alkyl dimethyl ammonium salt and the like, amphoteric surfactants such as alkyl dimethyl amine oxide, alkylcarboxybetaine and the like.

As for the surfactants, from the aspect of enhancing the transdermal absorbability, a non-ionic surfactant which is liquid at ambient temperature is preferable, sorbitan ester of fatty acid which is liquid at ambient temperature is more preferably, and sorbitan monolaurate is particularly preferable.

One or more kinds of surfactants can be used. The content of the surfactant is preferably 0.01 wt %-10 wt %, more preferably 0.1 wt %-5 wt %, relative to the total amount of the drug storage layer.

In the patch of the present invention, the drug storage layer and the adhesive layer may contain, as optional components, pharmaceutically conventional additives such as excipient, dispersing agent, stabilizer, viscous agent, antioxidant, softening agent, flavoring agent, colorant and the like, as long as the characteristics of the present invention are not impaired.

Examples of the excipient include silicon compound such as silicic anhydride, light anhydrous silicic acid, silicic hydride and the like; cellulose derivative such as ethylcellulose, methylcellulose, hydroxypropylcellulose, hydroxypropylmethylcellulose and the like; water-soluble synthesis polymer such as polyvinyl alcohol and the like; aluminum compound such as dried aluminum hydroxide gel, water-containing aluminum silicate and the like; pigment such as kaolin, titanium oxide and the like; and the like. One or more kinds of excipients can be used.

Examples of the dispersing agent include gum arabic, propylene glycol alginate, sodium dioctyl sulfosuccinate, lecithin and the like. One or more kinds of dispersing agents can be used.

Examples of the stabilizer include zinc stearate, gelatin, dextran, povidone and the like. One or more kinds of stabilizers can be used.

Examples of the viscous agent include carboxyvinyl polymer, xanthan gum, tragacanth, locust bean gum and the like. One or more kinds of viscous agents can be used.

Examples of the antioxidant include dibutylhydroxy-toluene, ascorbic acid stearic acid ester, tocopherol ester derivatives such as tocopherol acetate and the like, butylhydroxyanisole, 2-mercaptobenzimidazole, anthocyanin, catechin and the like. One or more kinds of antioxidants can be used.

Examples of the softening agent include fats and oils such as almond oil, rape seed oil, cottonseed oil-soybean oil mixture, process oil, beef tallow and the like; waxes such as purified lanolin and the like; esters which are solid at ambient temperature such as cetyl lactate and the like; rubbers such as polyisoprene rubber, polybutene, crude rubber and the like; polymer such as crystalline cellulose and the like; allantoin and the like. One or more kinds of softening agents can be used.

Examples of the flavoring agent include d-camphor, dl-camphor, d-borneol, dl-borneol, cinnamaldehyde, peppermint oil, dl-menthol, l-menthol and the like. One or more kinds of flavoring agents can be used.

Examples of the colorant include red ferric oxide, yellow iron oxide, yellow ferric oxide, carbon black and the like. One or more kinds of colorants can be used.

While the thickness of the drug storage layer of the patch of the present invention is not particularly limited, it is preferably 10-2000 μm, more preferably 20-1000 μm, to maintain sufficient drug content and not prevent adhesiveness. The mass per unit area of the drug storage layer is preferably 10-1000 $g/m^2$, more preferably 20-800 $g/m^2$.

In the patch of the present invention, the "support" is not particularly limited, and one widely used for patches can be used. For example, stretchable or non-stretchable woven fabric or non-woven fabric of polyethylene, polypropylene and the like, a film of polyethylene, polypropylene, polyester such as poly(ethylene terephthalate) and the like, ethylene vinyl acetate copolymer, vinyl chloride and the like, or a plastic foamed film of polyurethane and the like can be mentioned. A single kind of support may be used or a laminate of plural kinds thereof may be used. Furthermore, to prevent accumulation of static electricity on the support, an antistatic agent may be added to woven fabric, non-woven fabric, film and the like. Non-woven fabric or woven fabric, or a laminate of these and a film is preferable since it affords good anchor property between the support and the drug storage layer. The thickness of a film as the support is generally 10-100 μm, preferably 15-50 μm, and the thickness of woven fabric, non-woven fabric, and a porous sheet such as foamed film and the like is generally 50-2,000 μm, preferably 100-1,000 μm.

When a drug permeation control film is formed between a drug storage layer and an adhesive layer, the permeation control film is not particularly limited, and various polymer films (e.g., films such as polyolefins such as polyethylene, polypropylene and the like, polytetrafluoroethylene, polycarbonates, polyesters such as polyethylene terephthalate and the like, ethylenevinyl acetate copolymer, polyvinyl chloride, cellulose acetate, cellulose nitrate, polyacrylonitrile, polyurethane and the like) and the like can be mentioned. The polymer film is preferably porous, and the porosity is preferably 5-90%, more preferably 10-85%.

In addition, the patch of the present invention can also be provided with a release liner generally used in the field of patches. As the release liner, glassine; plastic films such as polyethylene, polypropylene, polyesters such as poly(ethylene terephthalate) and the like, polystyrene and the like; aluminum film; polyolefin foam films such as polyethylene foam film, polypropylene foam film and the like and the like can be mentioned, and any one kind or a laminate of plural kinds thereof can be used. Furthermore, these release liners that underwent peel treatment processing using silicone, fluororesin and the like, emboss processing, hydrophilic processing, hydrophobicity processing and the like, and the like can also be used. The thickness of the release liner is generally 10 μm-200 μm, preferably 15 μm-150 μm.

In the patch of the present invention, the drug storage layer can be obtained by, for example, dissolving a drug and components other than the drug in a solvent and applying and drying same on a support, or applying and drying same on a release liner to form a drug storage layer on the surface of the release liner, and thereafter adhering the support by pressing same on the drug storage layer. The adhesive layer can be obtained by dissolving each of a thermoplastic elastomer in a non-volatile hydrocarbon oil, dissolving or dispersing this in a solvent such as toluene and the like to prepare a coating liquid for forming an adhesive layer, applying the obtained coating liquid on the above-mentioned drug storage layer or release liner, and then drying same.

When an adhesive layer is formed on a release liner, a patch can be obtained by press adhering same to the drug storage layer. When a permeation control film is formed between a drug storage layer and an adhesive layer, for example, a patch may be obtained by preparing the first sheet wherein an adhesive layer is formed on a peel treated sheet (release liner) and the second sheet wherein a drug storage layer is formed on a support, laminating the first sheet on one surface of a permeation control film with the adhesive layer facing said one surface and laminating the second sheet on the other surface of the permeation control film with the drug storage layer facing said one surface. A coating liquid for forming a drug storage layer and an adhesive layer can be applied using, for example, a conventionally-used coater such as roll coater, die coater, gravure roll coater, reverse roll coater, kiss-roll coater, dip roll coater, bar coater, knife coater, spray coater and the like. In addition, the aforementioned solution is preferably dried under heating at, for example, about 40° C.-150° C.

EXAMPLES

The present invention is explained in more detail in the following by referring to Examples and Comparative Examples, which are not to be construed as limitative.

Example 1

Preparation of Patch Containing Rivastigmine

According to the formulation shown in Table 1, each component constituting a drug storage layer was weighted. First, a styrene-isoprene-styrene block copolymer ("SIS D1119", manufactured by Kraton Performance Polymers Inc., weight average molecular weight=207,500) was dissolved in toluene at a ratio of 100 parts by weight of the styrene-isoprene-styrene block copolymer in 230 parts by weight of toluene. To the aforementioned dissolution were added liquid paraffin ("Hydrobrite HV", manufactured by Sonneborn Ltd., kinematic viscosity: 247 mm$^2$/s) and rivastigmine, and they were mixed and stirred to prepare a coating liquid for drug storage layer formation.

The above-mentioned coating liquid was applied onto a silicone-treated polyethylene terephthalate (PET) film (release liner) such that the content of rivastigmine in the drug storage layer after drying was 1.8 mg/cm$^2$. After drying in an oven at 80° C. for 1 hr, a PET film (support) was laminated on a surface of the drug storage layer to give the object drug storage layer.

On the other hand, according to the formulation shown in Table 1, each component constituting the adhesive layer was weighed. First, a styrene-isoprene-styrene block copolymer ("SIS D1119", manufactured by Kraton Performance Polymers Inc., weight average molecular weight=207,500) was dissolved in toluene at a ratio of 100 parts by weight of the styrene-isoprene-styrene block copolymer in 230 parts by weight of toluene. To the aforementioned dissolution was added liquid paraffin ("Hydrobrite HV", manufactured by Sonneborn Ltd.), they were mixed and stirred to prepare a coating liquid for an adhesive layer formation.

The above-mentioned coating liquid was applied onto a silicone-treated polyethylene terephthalate (PET) film (release liner) such that the weight of the adhesive layer weight after drying was 100 g/m$^2$. After drying in an oven at 80° C. for 1 hr, the drug storage layer was laminated on a surface of the adhesive layer, which was cut in the size of 15 cm×30 cm to give the object patch.

TABLE 1

| component | | drug storage layer | adhesive layer |
|---|---|---|---|
| thermoplastic elastomer | styrene-isoprene-styrene block copolymer | 28.5 | 30 |
| non-volatile hydrocarbon oil | liquid paraffin | 66.5 | 70 |
| | rivastigmine | 5 | — |

*1; Numerical values in Table show content (wt %) in drug storage layer and adhesive layer.

Comparative Example 1

In the formulation of the adhesive layer of Example 1 in Table 1, a commercially available heat-curable pressure-sensitive acrylic adhesive ("Duro tak 87-2194", manufactured by Henkel Japan Ltd., solid content=40 wt %) was weighed instead of the styrene-isoprene-styrene block copolymer, such that the solid content was the same as the thermoplastic elastomer content in Table 1, liquid paraffin was added, and the mixture was stirred to give a coating liquid for forming an adhesive layer.

The coating liquid was applied on a silicone-treated PET film (release liner), prepared such that the weight of the adhesive layer after drying was 100 g/m$^2$ and dried in an oven at 80° C. for 60 min. However, the liquid was not hardened and a patch could not be obtained.

Comparative Examples 2, 3

According to the formulations shown in Table 2, each component constituting the adhesive layer was measured, and a patch was prepared in the same manner as in Example 1. As for Comparative Example 2, sufficient adhesiveness was not obtained and, as for Comparative Example 3, the adhesive layer could not be maintained and evaluation was not possible.

TABLE 2

| component | | Comparative Examples 2 adhesive layer | Comparative Examples 3 adhesive layer |
|---|---|---|---|
| thermoplastic elastomer | styrene-isoprene-styrene copolymer | 70 | 10 |
| non-volatile hydrocarbon oil | liquid paraffin | 30 | 90 |
| | rivastigmine | — | — |

*1; Numerical values in Table show content (wt %) in adhesive layer.

Experimental Example 1

In Vitro Skin Permeability Test

According to the method described in WO 2006/093139, the skin extracted from the abdomen of a male Wister rat (5-week-old) was set on a vertical Franz diffusion cell. Commercially available rivastigmine-containing patches (rivastigmine content=1.8 mg/cm$^2$) wherein a drug layer and an adhesive layer are formed on the patch and the support of Example 1 were each punched out in a circular shape with area 1.0 cm$^2$ to give samples, which were adhered to the rat skin on the diffusion cell (n=3). On the receptor side, the content of rivastigmine in the receptor solution was measured over time by high performance liquid chromatography (HPLC) using 10% by volume ethanol saline. The measurement conditions of HPLC are shown below.

<HPLC Measurement Conditions>

HPLC system: high performance liquid chromatograph (LC2010C) manufactured by SHIMADZU CORPORATION
    column: ODS, 4.6 mmφ×15 cm, 5 μm
    column temperature: 25° C.
    mobile phase: buffer/methanol=50/50
    (buffer; 5.0 mM sodium 1-heptane sulfonate, 1% by volume phosphoric acid)
    detection wavelength: 220 nm
    flow: 0.8 mL/min In the above-mentioned skin permeability test, the amount of rivastigmine that permeated the rat skin was determined 24 hr after adhesion of the sample and shown in Table 3.

TABLE 3

| patch | amount of rivastigmine that permeated skin in 24 hr after adhesion of sample (μg/cm²) |
|---|---|
| Example 1 | 380 |
| commercially available rivastigmine-containing patch | 360 |

From Table 3, it was shown that the amount of the patch of Example 1 of the present invention was almost equivalent to that of the commercially available rivastigmine-containing patch having the same rivastigmine content per unit area, thus showing good skin permeability of the present invention.

Example 2

Preparation of Patch Containing Clonidine

According to the formulation shown in Table 4, each component constituting the drug storage layer was weighted. First, to clonidine and light liquid paraffin ("Lytol", manufactured by Sonneborn Ltd., kinematic viscosity: 4.46 mm²/s) was added heptane at a ratio of 300 parts by weight of heptane relative to 100 parts by weight of the components forming the drug storage layer, and the mixture was homogenized using a Polytron homogenizer at 5000-10000 rpm for 10 min. Then, a mixture of high molecular weight polyisobutylene ("Oppanol B100", manufactured by BASF, weight average molecular weight 1,110,000) and low molecular weight polyisobutylene ("Oppanol B10SFN", manufactured by BASF, weight average molecular weight 40,000) at a mixing ratio of 5.2/6.5 (weight ratio) was added to a homogenized mud-like product, and they were mixed and stirred at a low shear until clonidine particles were suspended and polyisobutylenes were dissolved to prepare a coating liquid for drug storage layer formation.

The above-mentioned coating liquid was applied onto an aluminum-treated polyethylene terephthalate (PET) film (support) such that the drug storage layer after drying was about 50 μm thick, air-dried overnight and dried in an oven at 60° C. for 15 min to give the object drug storage layer.

According to the formulation shown in Table 4, each component constituting the adhesive layer was weighted. First, a styrene-isoprene-styrene block copolymer ("JSR SIS5505", manufactured by JSR) was dissolved in toluene at a ratio of 300 parts by weight of heptane relative to 100 parts by weight of the styrene-isoprene-styrene block copolymer. To the aforementioned dissolution were added clonidine and liquid paraffin ("Hydrobrite HV", manufactured by Sonneborn Ltd.), and they were mixed and stirred to prepare a coating liquid for adhesive layer formation.

The above-mentioned coating liquid was applied onto a silicone-treated poly(ethylene terephthalate) (PET) film (release liner) such that the weight of the adhesive layer after drying was about 70 μm thick, air-dried overnight, and dried in an oven at 60° C. for 15 min to give the object adhesive layer.

The above-mentioned adhesive layer was laminated on one surface of a 25 μm thick porous polypropylene film ("Celgard 2400", manufactured by Celgard LLC, porosity 41%) saturated by immersing in the above-mentioned light liquid paraffin, the above-mentioned drug storage layer was laminated on the other surface. The laminate was cut into the size of 15 cm×30 cm to give the object patch. The content of clonidine in the obtained patch was 0.73 mg/cm².

TABLE 4

| | component | drug storage layer | adhesive layer |
|---|---|---|---|
| thermoplastic elastomer | styrene-isoprene-styrene block copolymer | | 30.0 |
| | polyisobutylene | 46.8 | |
| non-volatile hydrocarbon oil | light liquid paraffin | 41.6 | |
| | liquid paraffin | | 66.4 |
| | clonidine | 11.6 | 3.6 |

* Numerical values in Table show contents (wt %) in drug storage layer and adhesive layer.

Experimental Example 2

Skin Permeability Test In Vitro

According to the method described in WO 2006/093139, the skin extracted from the abdomen of a male Wister rat (5-week-old) was set on a vertical Franz Diffusion Cell. The patch of Example 2 was punched out in a circular shape (area 0.5 cm²) to give a sample. Similarly, a circular sample with an area 0.75 cm² and a circular sample with an area 1 cm² were obtained. A commercially available clonidine-containing patch (clonidine content=0.71 mg/cm²) wherein a drug storage layer and an adhesive layer were formed on a support was punched out to give a circular sample with area 1 cm². The samples were adhered onto the rat skin on the diffusion cell (n=3), 10% by volume ethanol saline was used on the receptor side, and the content of rivastigmine in the receptor solution was quantified over time by high performance liquid chromatography (HPLC). The HPLC measurement conditions are shown below.

<HPLC Measurement Condition>

HPLC system: high-speed liquid chromatography (LC2010C) manufactured by Shimadzu Corporation
    column: ODS, 4.6 mmφ×15 cm, 5 μm
    column temperature: 40° C.,
    mobile phase: buffer/acetonitrile/methanol=40/50/10, sodium dodecylsulfate 0.9 g
    (buffer; 30.1 v/v % aqueous phosphoric acid solution)
    detection wavelength: 215 nm,
    flow: 0.7 mL/min.

In the above-mentioned skin permeability test, the amount of clonidine that permeated the rat skin up to 168 hr after adhesion of the sample was regularly quantified, and the cumulative permeation amount and permeation amount per unit time was calculated. The results are shown in FIG. 1 and FIG. 2.

Figure 2:
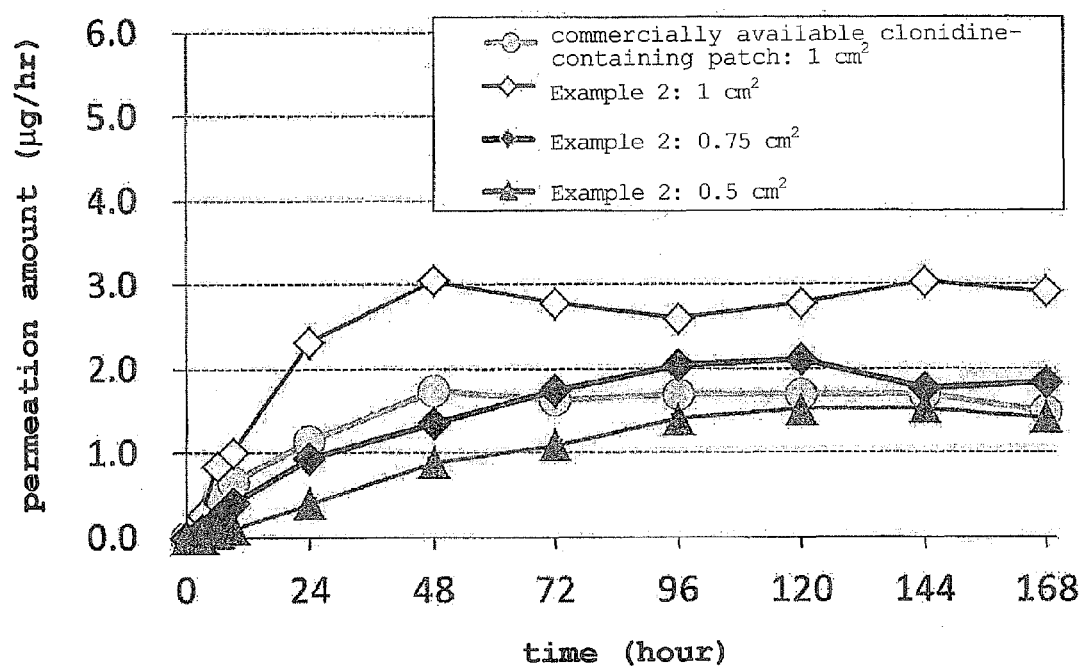
FIG. 2 shows a permeation amount per unit time of clonidine that permeated the rat skin in the skin permeability test in Experimental Example 2.

From FIG. 1 and FIG. 2, it is clear that the patch of Example 2 of the present invention has about 1.5-fold higher skin permeability as compared to a commercially available clonidine-containing patch having the same clonidine content per unit area, and shows skin permeability equivalent to that of a commercially available product in the 75% area of the commercially available product. In addition, like the commercially available products, skin permeability was maintained at a given level until 168 hr after adhesion, and it was shown that the skin permeability of the preparation of Example 2 was fine.

Experimental Example 3

Primary Skin Irritation Test

Three days before the start of adhesion, dorsal hair of kbs: JW female domestic rabbit (17-week-old) was shaven with an electric clipper, and the patch of Example 1 and a commercially available rivastigmine-containing patch which were each cut into a 2.5 cm square were adhered to the skin, (n=3). Oil paper was placed thereon to cover the adhesion site, an underlap tape (manufactured by Nichiban Co., Ltd.) was wound from the chest to the whole abdomen, and a jacket for domestic rabbit (BJ03, manufactured by Bioresearch Center Co., Ltd.) was set thereon. After fixing for 24 hr, the sample was removed, and the level of skin irritation reaction was evaluated based on the method described in J. Pharmacol. Exp. Ther. 82, 377-390 (1944) at 1 hr, 24 hr, 48 hr and 72 hr after the removal.

That is, at each of the above-mentioned times, erythema and eschar formation and edema formation were evaluated according to the following evaluation criteria, and scored. An average of respective evaluation points was determined, the primary evaluation value was calculated, and an average of the average evaluation value at each of the above-mentioned times was determined for each domestic rabbit and taken as a primary irritation index (P.I.I.). The P.I.I. value was 0 at the lowest and 8 at the highest, and the values are divided into 4 categories of primary skin irritation reaction shown in Table 5.

<Evaluation Criteria of Skin Irritation Reaction>
[Formation of Erythema and Eschar]
  no erythema; 0 point
  very slight (barely perceptible level of) erythema; 1 point
  well-defined erythema; 2 points
  moderate to severe erythema; 3 points
  severe erythema to eschar formation of level preventing erythema scoring; 4 points
[Formation of Edema]
  no edema; 0 point
  very slight (barely perceptible level of) edema; 1 point
  slight edema (edges of area well defined by definite rising); 2 points
  moderate edema (raised approximately 1 mm); 3 points
  severe edema (raised more than 1 mm and extending beyond exposure area); 4 points

TABLE 5

| category of skin primary stimulation reaction | P.I.I. |
|---|---|
| no stimulation | 0-0.4 |
| weak stimulation | 0.5-1.9 |
| moderate stimulation | 2-4.9 |
| strong stimulation | 5-8 |

The results of the skin primary stimulation test are shown in Table 6.

TABLE 6

| | P.I.I |
|---|---|
| Example 1 | 0 |
| commercially available rivastigmine-containing patch | 2.92 |

From Table 6, the commercially available rivastigmine-containing patch showed P.I.I. value of 2.92, thus showing the moderate level stimulation. In contrast, the patch of the Example 1 showed P.I.I. value of 0 and were evaluated to have no stimulation, thus showing low skin irritation.

INDUSTRIAL APPLICABILITY

As described in detail above, the present invention can provide a patch of a drug having sufficient skin adhesiveness and low skin irritation, showing good skin permeability of a drug, and sufficient transdermal absorbability.

This application is based on patent application No. 2012-230284 filed in Japan, the contents of which are incorporated in full herein.

The invention claimed is:

1. A transdermal patch having a laminate structure comprising a support layer, a drug storage layer, and an adhesive layer, in that order,
    wherein the adhesive layer comprises at least
        a thermoplastic elastomer, and
        a non-volatile hydrocarbon oil having a kinematic viscosity at 40° C. of not less than 60 mm$^2$/s in more than 50 parts by weight and not more than 800 parts by weight per 100 parts by weight of the thermoplastic elastomer, and
        the adhesive layer optionally further comprises a tackifier at a content of not more than 10 wt %, and
    wherein the drug storage layer comprises at least
        a drug,
        a thermoplastic elastomer or a polyisobutylene, and
        a non-volatile hydrocarbon oil having a kinematic viscosity at 40° C. of less than 60 mm$^2$/s.

2. The transdermal patch according to claim 1, wherein the content of the non-volatile hydrocarbon oil in the adhesive layer is not less than 23.5 wt % and not more than 88 wt %.

3. The transdermal patch according to claim 1, wherein the non-volatile hydrocarbon oil in the adhesive layer and the drug storage layer is liquid paraffin.

4. The transdermal patch according to claim 1, wherein the thermoplastic elastomer in the adhesive layer and the drug storage layer is a styrene-based block copolymer.

5. The transdermal patch according to claim 4, wherein the styrene-based block copolymer is a styrene-isoprene-styrene block copolymer.

6. The transdermal patch according to claim 1, wherein the adhesive layer is free of a tackifier.

7. The transdermal patch according to claim 1, wherein the drug is one or more kinds selected from the group consisting of rivastigmine, clonidine, rotigotine, and buprenorphine.

8. The transdermal patch according to claim 1, wherein the drug is clonidine or rivastigmine.

9. The transdermal patch according to claim 1, wherein the drug is rivastigmine.

10. The transdermal patch according to claim 5, wherein the adhesive layer is free of a tackifier.

11. The transdermal patch according to claim 10, wherein the drug is one or more kinds selected from the group consisting of rivastigmine, clonidine, rotigotine, and buprenorphine.

12. The transdermal patch according to claim 10, wherein the drug is clonidine or rivastigmine.

13. The transdermal patch according to claim 10, wherein the drug is rivastigmine.

* * * * *